(12) United States Patent
Thibault Pelletier et al.

(10) Patent No.: US 11,179,131 B2
(45) Date of Patent: Nov. 23, 2021

(54) RADIATION FLUOROSCOPIC IMAGING APPARATUS

(71) Applicant: Shimadzu Corporation, Kyoto (JP)

(72) Inventors: David Thibault Pelletier, Laval (CA); Naoki Hasegawa, Kyoto (JP); Keiichi Tanno, Kyoto (JP); Takaya Yamamoto, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 141 days.

(21) Appl. No.: 16/807,993

(22) Filed: Mar. 3, 2020

(65) Prior Publication Data

US 2020/0315564 A1 Oct. 8, 2020

(30) Foreign Application Priority Data

Apr. 3, 2019 (JP) .............................. JP2019-071327

(51) Int. Cl.
| | |
|---|---|
| *A61B 6/00* | (2006.01) |
| *G06T 7/00* | (2017.01) |
| *G06T 5/00* | (2006.01) |
| *G01N 23/04* | (2018.01) |

(52) U.S. Cl.
CPC ............ *A61B 6/5241* (2013.01); *A61B 6/463* (2013.01); *A61B 6/481* (2013.01); *A61B 6/487* (2013.01); *A61B 6/504* (2013.01); *A61B 6/54* (2013.01); *G01N 23/043* (2013.01); *G06T 5/003* (2013.01); *G06T 7/0012* (2013.01); *G01N 2223/401* (2013.01); *G06T 2207/10121* (2013.01); *G06T 2207/30101* (2013.01)

(58) Field of Classification Search
None
See application file for complete search history.

(56) References Cited

U.S. PATENT DOCUMENTS

| | | | |
|---|---|---|---|
| 5,671,743 A | 9/1997 | Kawai et al. | |
| 2004/0114717 A1* | 6/2004 | Kato | ........................ G06T 5/007 378/62 |
| 2010/0183116 A1* | 7/2010 | Zaiki | ...................... A61B 6/481 378/8 |
| 2013/0094734 A1* | 4/2013 | Rauch | ........................ G06T 7/38 382/130 |
| 2017/0164921 A1 | 6/2017 | Hirose et al. | |
| 2017/0295300 A1* | 10/2017 | Esashi | .................... A61B 6/504 |

FOREIGN PATENT DOCUMENTS

| | | |
|---|---|---|
| JP | 2927209 B2 | 5/1999 |
| JP | 2010-162278 A | 7/2010 |
| JP | 2017-104538 A | 6/2017 |

\* cited by examiner

*Primary Examiner* — Hoon K Song
(74) *Attorney, Agent, or Firm* — Muir Patent Law, PLLC (57) ABSTRACT

In this radiation fluoroscopic imaging apparatus, an image processing unit is configured to generate a first image by performing first image processing that clarifies a blood vessel as an imaging target when capturing a plurality of contrast agent images and generate a plurality of second images used to generate a differential long image by performing second image processing.

8 Claims, 10 Drawing Sheets

RADIATION FLUOROSCOPIC IMAGING APPARATUS

CROSS-REFERENCE TO RELATED APPLICATIONS

The related application number JP2019-071327, entitled "radiation fluoroscopic imaging apparatus", filed on Apr. 3, 2019, and invented by David Thibault Pelletier, Naoki Hasegawa, Keiichi Tannno, and Takaya Yamamoto upon which this patent application is based is hereby incorporated by reference.

BACKGROUND OF THE INVENTION

Field of the Invention

The present invention relates to a radiation fluoroscopic imaging apparatus and, more particularly, to a radiation fluoroscopic imaging apparatus for generating a differential long image.

Description of the Background Art

Conventionally, an X-ray diagnostic apparatus configured to generate a differential long image by irradiating a subject with X-rays has been known. Such a radiation fluoroscopic imaging apparatus is disclosed in, for example, Japanese Unexamined Patent Application Publication No. 2010-162278.

In the X-ray image diagnostic apparatus described in the above-mentioned Japanese Unexamined Patent Application Publication No. 2010-162278, X-ray imaging is performed while relatively moving a detector and a subject to acquire an X-ray image group, and a long image is generated by superimposing parts of the acquired X-ray image group. The X-ray image diagnosis apparatus disclosed in Japanese Unexamined Patent Application Publication No. 2010-162278 includes a DSA (digital subtraction angiography) image capturing mode, generates a differential image (DSA image) which is a blood vessel image by subjecting an X-ray transmission image (mask image) not including a contrast agent image and an X-ray transmission image (contrast image or live image) including a contrast agent image to subtraction processing and displays and stores the DSA image. Further, the X-ray image diagnostic apparatus described in the above-mentioned Japanese Unexamined Patent Application Publication No. 2010-162278 collects live images after collecting mask images. Further, the X-ray image diagnostic apparatus described in the above-mentioned Japanese Unexamined Patent Application Publication No. 2010-162278 generates a long image based on the acquired DSA image.

SUMMARY OF THE INVENTION

Although not disclosed in the above-mentioned Japanese Unexamined Patent Application Publication No. 2010-162278, conventionally, a contrast agent image (live image) is captured in a state in which a contrast agent is sufficiently included in a blood vessel at an image capturing position in order to clearly image a blood vessel. Therefore, it is required to capture a contrast agent image by relatively moving the detector and the subject in accordance with the timing at which the contrast agent moves.

However, an X-ray diagnostic imaging apparatus as disclosed in Japanese Unexamined Patent Application Publication No. 2010-162278 has a problem that a desired differential long image cannot be appropriately generated. That is, in the X-ray image diagnostic apparatus as disclosed in Japanese Unexamined Patent Application Publication No. 2010-162278, after capturing a contrast agent image (live image) and a non-contrast agent image (mask image), subtraction processing (differential processing) is performed to acquire a differential image which is a blood vessel image in which a blood vessel is made clear. For this reason, no differential image is generated at the time of capturing a contrast agent image. Therefore, at the time of capturing a contrast agent image, it is required to confirm whether or not a contrast agent is sufficiently included in a blood vessel based on not the differential image but the acquired contrast agent image. However, since the contrast agent image includes portions other than a blood vessel, there are drawbacks that the visibility is poor and the movement of the contrast agent cannot be clearly confirmed. In cases where the movement of the contrast agent cannot be clearly confirmed, the detector and the subject cannot be moved relatively in accordance with the timing of the movement of the contrast agent, and therefore there is a possibility that an appropriate contrast agent image used to generate a differential long image cannot be acquired.

On the other hand, there are the following problems also at the time of capturing a non-contrast agent image. That is, in the X-ray image diagnostic apparatus as disclosed in Japanese Unexamined Patent Application Publication No. 2010-162278, since a contrast agent image is captured after capturing a non-contrast agent image, a blood vessel cannot be confirmed at the time of capturing a non-contrast agent image. Therefore, for example, when a subject is arranged at an unintended position with respect to the relative positional relationship between the detector and the subject, the image capturing of the non-contrast agent image is performed without noticing the unintended position. As a result, re-imaging is required, resulting in an increased exposure dose to the subject.

The present invention has been made to solve the above-mentioned problems, and an object of the present invention is to provide a radiation fluoroscopic imaging apparatus capable of appropriately generating a desired differential long image.

In order to achieve the above object, a radiation fluoroscopic imaging apparatus according to one aspect of the present invention includes:

an imaging unit including a radiation source configured to emit radiation to a subject and a detection unit configured to detect radiation emitted from the radiation source and transmitted through the subject and acquire a detection signal;

an image processing unit configured to generate a plurality of contrast agent images based on the detection signal acquired at a plurality of relative positions using a contrast agent, generate a plurality of non-contrast agent images based on the detection signal acquired at the plurality of relative positions without using a contrast agent, and generate a differential long image by subjecting the non-contrast agent images and the contrast agent images to subtraction processing and connection processing; and a control unit configured to perform control to output an image generated by the image processing unit and display the image on a display unit, wherein the image processing unit is configured to, when capturing the plurality of contrast agent images while changing a relative position between the imaging unit and the subject, generate a first image by performing first image processing that clarifies a blood vessel as an imaging target on the plurality of contrast agent images and generate the plurality of second images used to generate the differential long image by performing second image processing that reduces a pixel value difference of a portion of the subject common to the contrast agent image and the non-contrast image, and wherein the control unit is configured to perform control to sequentially display the first image corresponding to each of the plurality of contrast agent images when capturing the plurality of contrast agent images while changing the relative position between the imaging unit and the subject.

According to the present invention, in the radiation fluoroscopic imaging apparatus, the image processing unit is configured to generate a first image by performing first image processing that clarifies a blood vessel as an imaging target on a plurality of contrast agent images, and the control unit is configured to sequentially display the first image corresponding to each of contrast agent images at the time of capturing a plurality of contrast agent images while changing a relative position between the imaging unit and the subject and perform control to generate a plurality of second images used to generate a differential long image by performing second image processing that reduces a pixel value difference of a portion of the subject common to the contrast agent image and the non-contrast agent image. With this, at the time of capturing a plurality of contrast agent images while changing the relative position between the imaging unit and the subject, a first image in which a blood vessel as an imaging target corresponding to each of contrast agent images is made clear is generated and displayed. Therefore, the user can clearly confirm the moving of the contrast agent in the blood vessel at the time of capturing a contrast agent image. In addition, by generating a plurality of second images used to generate a differential long image, a differential image can be generated at the time of capturing a non-contrast agent image, so that a blood vessel can be confirmed at the time of capturing a non-contrast agent image. As a result, it is possible to provide a radiation fluoroscopic imaging apparatus capable of appropriately generating a desired differential long image.

DESCRIPTION OF THE PREFERRED EMBODIMENT

Hereinafter, embodiments in which the present invention is embodied will be described with reference to the attached drawings.

This Embodiment

Referring to FIG. 1 to FIG. 10, the configuration of the X-ray fluoroscopic imaging apparatus 100 according to this embodiment will be described. Note that the X-ray fluoroscopic imaging apparatus 100 is an example of the "radiation fluoroscopic imaging apparatus" recited in claims.

(Configuration of X-Ray Fluoroscopic Imaging Apparatus)

Figure 1:
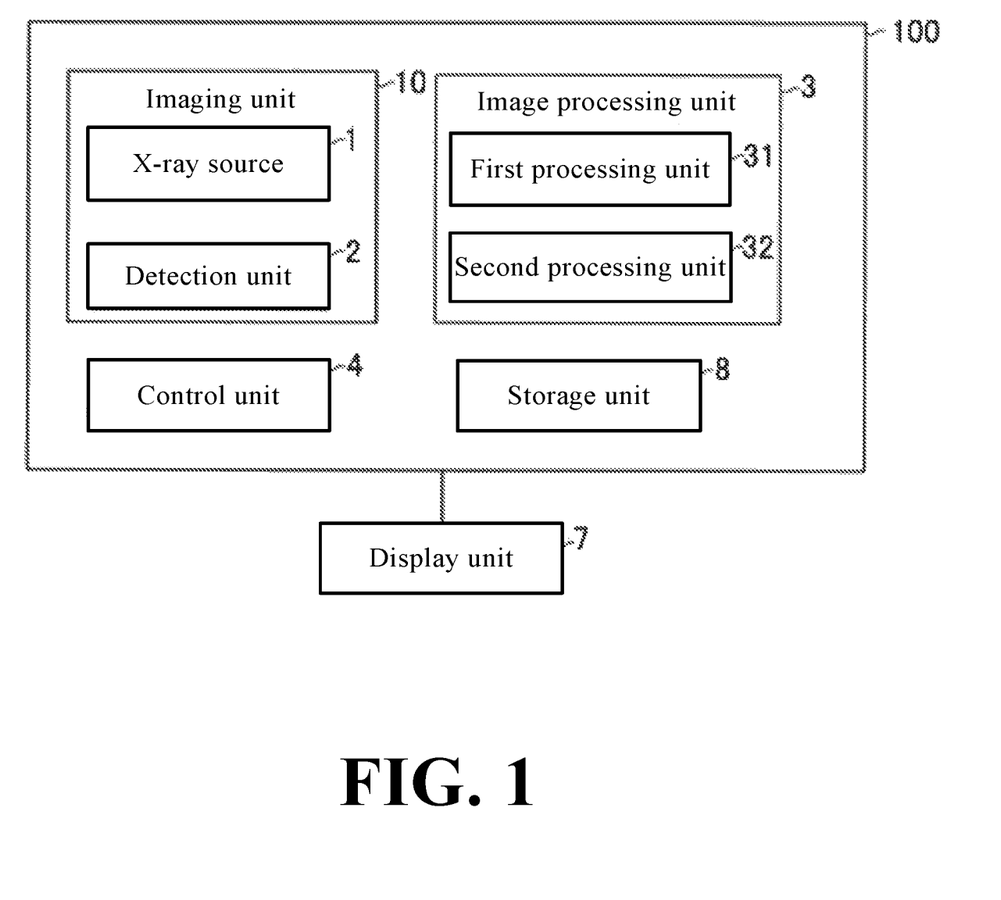
FIG. 1 is a block diagram showing a configuration of an X-ray fluoroscopic imaging apparatus.

As shown in FIG. 1, the X-ray fluoroscopic imaging apparatus 100 of this embodiment is provided with an imaging unit 10 including an X-ray source 1 and a detection unit 2, an image processing unit 3, and a control unit 4.

Figure 2:
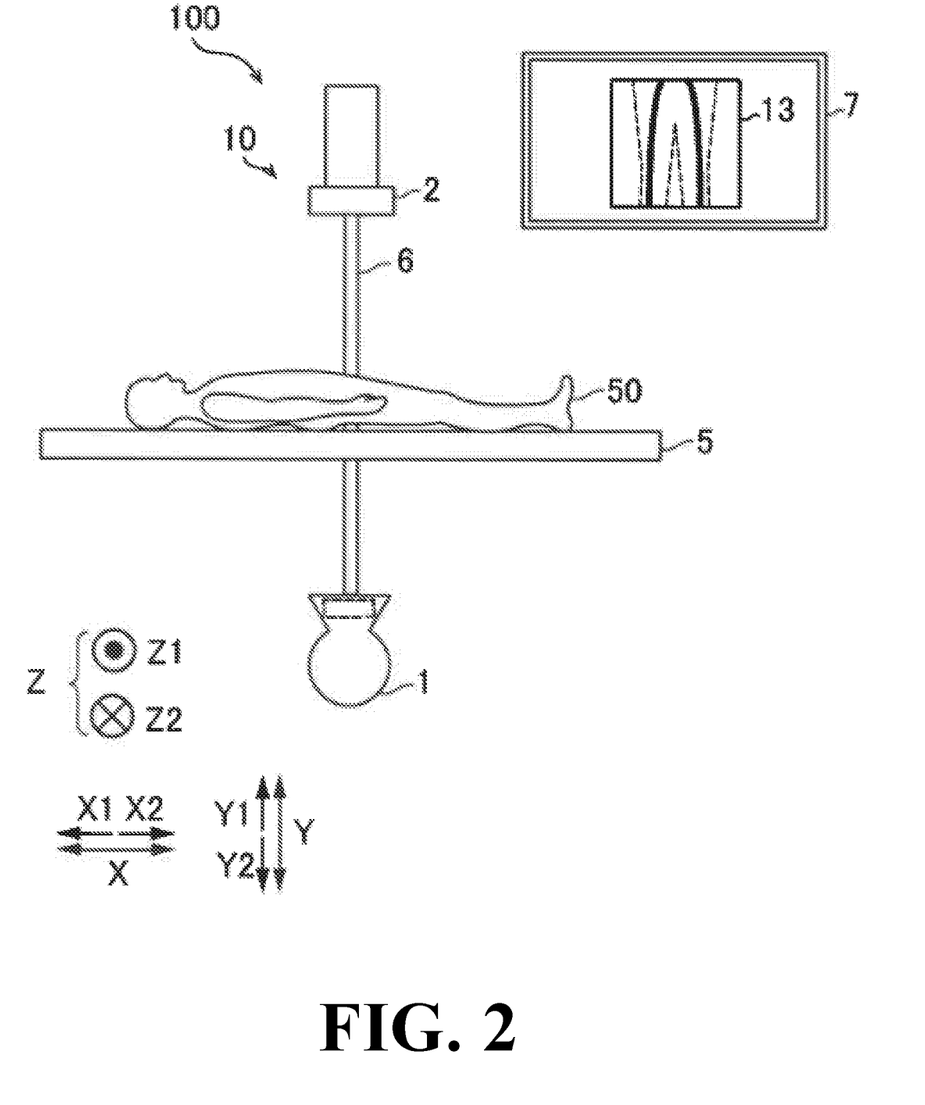
FIG. 2 is a diagram illustrating an example of an X-ray fluoroscopic imaging apparatus.

As shown in FIG. 2, the X-ray fluoroscopic imaging apparatus 100 of this embodiment is configured to irradiate a subject 50 placed on a top board 5 with X-rays from an X-ray source 1.

The top board 5 is formed in a rectangular flat plate shape in a plan view. The subject 50 is placed on the top board 5 such that the head-foot direction of the subject 50 is along the long side of the rectangle and the left-right direction of the subject 50 is along the short side of the rectangle. Note that in this specification, the head-foot direction of the subject 50 is defined as an X-direction, the left-right direction of the subject 50 is defined as a Z-direction, and the direction perpendicular to the X-direction and the Z-direction is defined as a Y-direction.

The X-ray source 1 is arranged on one side of the top board 5 in the Y-direction. The X-ray source 1 can emit X-rays when voltage is applied by a drive unit (not shown). The X-ray source 1 has a collimator capable of adjusting the irradiation field of X-rays which is an irradiation range. In this embodiment, the X-ray source 1 is attached to the tip end of an arm 6 on one side (Y2-direction side).

The detection unit 2 is attached to the tip end of the arm 6 on the other side (opposite side of the X-ray source 1). That is, the detection unit 2 is arranged on the opposite side of the X-ray source 1 with the top board 5 interposed therebetween. The detection unit 2 is configured to detect X-rays. The detection unit 2 is, for example, an FPD (flat panel detector).

As shown in FIG. 1, the image processing unit 3 is a computer configured to include a processor, such as, e.g., a GPU (Graphics Processing Unit) and an FPGA (Field-Programmable Gate Array) configured to process images. The image processing unit 3 functions as an image processing apparatus by executing an image processing program.

As shown in FIG. 1, the image processing unit 3 includes a first processing unit 31 and a second processing unit 32. The first processing unit 31 is configured to perform first image processing 33 and fourth image processing 36. The second processing unit 32 is configured to perform second image processing 34 and third image processing 35.

As shown in FIG. 1, the control unit 4 is a computer configured to include a CPU (Central Processing Unit), a ROM (Read Only Memory), and a RAM (Random Access Memory).

The X-ray fluoroscopic imaging apparatus 100 of this embodiment is provided with a display unit 7 and a storage unit 8. In this embodiment, the display unit 7 is a monitor installed in an examination office or the like where X-ray fluoroscopic imaging is performed. The control unit 4 is configured to output a first image 13 and a differential image 17 to the display unit 7 (see FIG. 3).

The storage unit 8 is provided with a CPU and a ROM provided in the control unit 4. The storage unit 8 is configured to store a second image 14 generated by the image processing unit 3.

The X-ray fluoroscopic imaging apparatus 100 is used to capture images for diagnosing the subject 50. In this embodiment, the target portion is a blood vessel 50a of a lower limb of the subject 50.

Since the blood vessel 50a of the lower limb extends from the foot base to the toe of the subject 50, it is not possible to capture the entire image in a single imaging operation. Therefore, a differential long image 18 in which a plurality of images is connected together is used for medical examinations.

Figure 10:
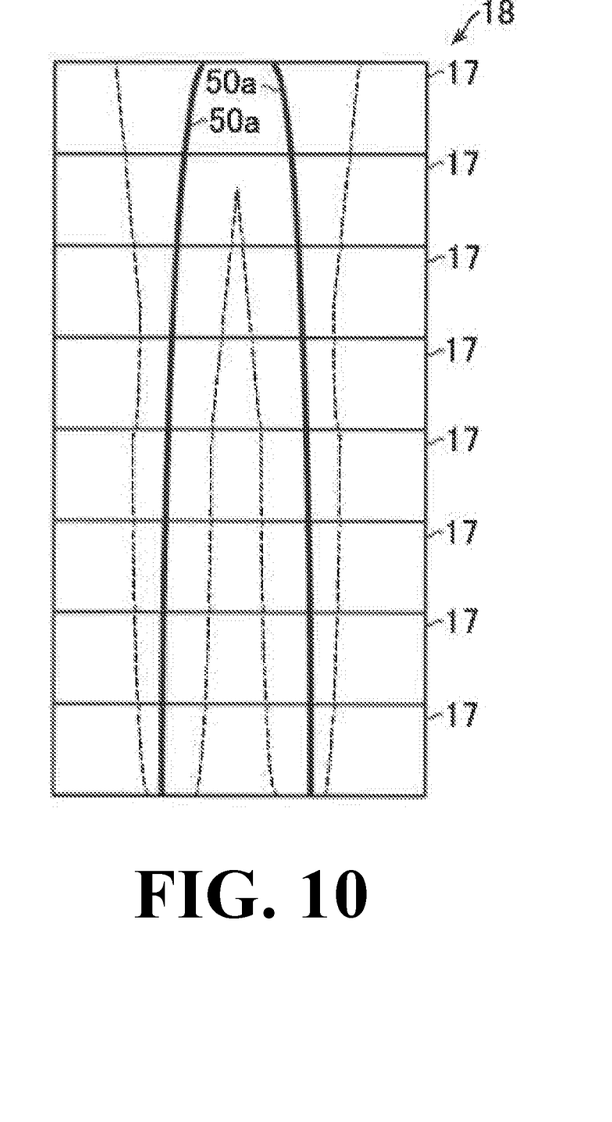
FIG. 10 is a diagram illustrating a differential long image.

As shown in FIG. 10, a differential long image 18 is generated by connecting a plurality of differential images 17 obtained in the order of the relative position coordinates of the top board 5 based on the relative position coordinates of the top board 5 by subjecting a plurality of contrast agent images 11 and a plurality of non-contrast agent images 12 having the same relative position coordinate to subtraction processing.

Figure 4:
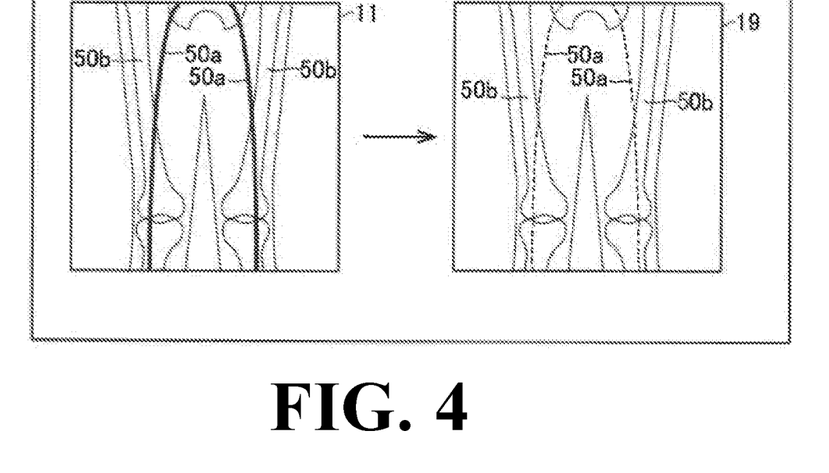
FIG. 4 is a diagram for explaining generation of a defocus image.

As shown in FIG. 4, the contrast agent image 11 is an image in which a blood vessel 50a is imaged. Here, the portion such as the blood vessel 50a where the attenuation rate of irradiated X-rays does not differ from that of the surrounding tissue is uncleared in the X-ray image in a state in which no contrast agent has been administered. Therefore, by administering a contrast agent that shields X-rays and changes the attenuation rate of X-rays, the blood vessel 50a to which a contrast agent has been administered differs in the attenuation rate of the irradiated X-rays from the attenuation rate of X-rays emitted to the surrounding tissue, so that the contrast is generated and therefore the imaging can be performed.

Figure 7:
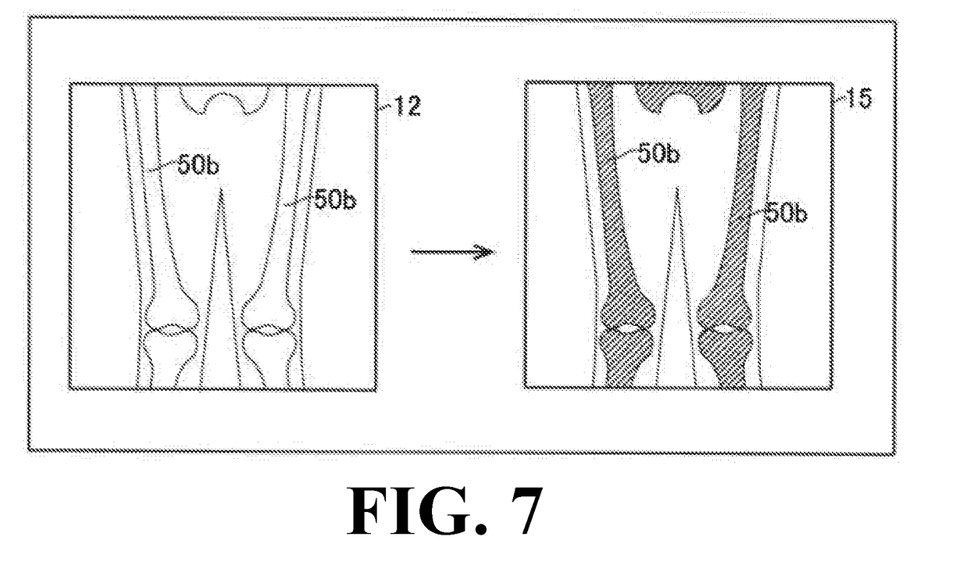
FIG. 7 is a diagram for explaining generation of a third image.

As shown in FIG. 7, the non-contrast agent image 12 is an image captured in a state in which no contrast agent has been administered to the subject 50. Therefore, the blood vessel 50a is unclear compared with the contrast agent image 11. The same non-contrast agent images except that whether or not the blood vessel 50a is clearly reflected can be generated by making the imaging condition to the same imaging condition of the contrast agent image 11.

Figure 8:
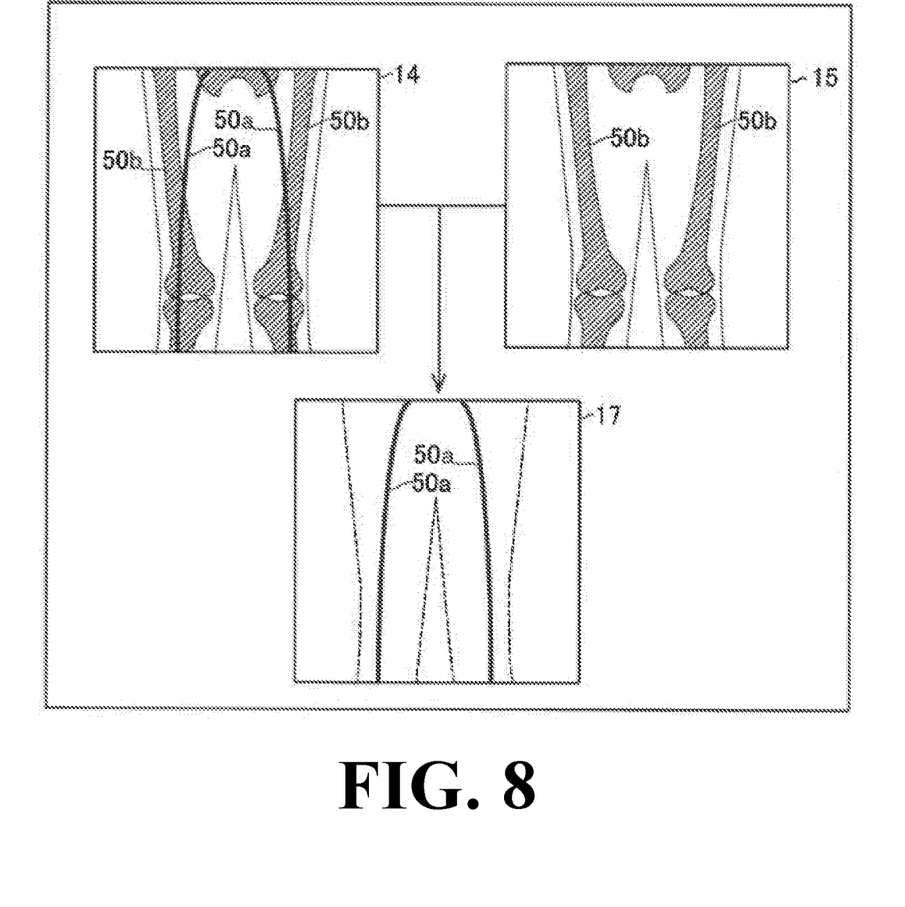
FIG. 8 is a diagram for explaining generation of a DSA image.

As shown in FIG. 8, a differential image 17 is an image in which a common portion other than the blood vessel 50a is made unclear and the blood vessel 50a is made clear by subjecting the contrast agent image 11 and the non-contrast agent image 12 to subtraction processing.

(Generating of Differential Long Image)

With reference to FIG. 3 to FIG. 10, generation of the differential long image 18 by the X-ray fluoroscopic imaging apparatus 100 according to this embodiment will be described.

Figure 3:
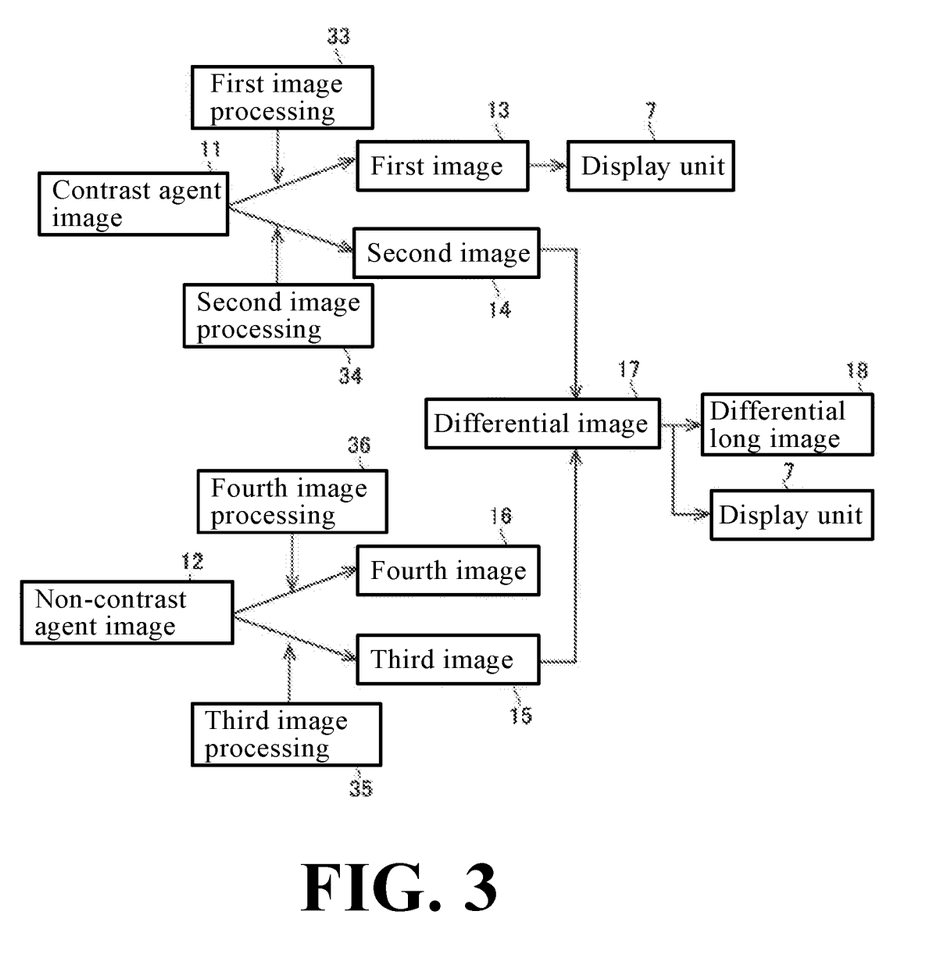
FIG. 3 is a diagram for explaining a flow of generation of a differential long image of an image processing unit.

As shown in FIG. 3, the image processing unit 3 is configured to generate images including a contrast agent image 11, a non-contrast agent image 12, a first image 13, a second image 14, a third image 15, a fourth image 16, a differential image 17, and a differential long image 18 based on detection signals from the detection unit 2.

As shown in FIG. 2 and FIG. 3, the contrast agent image 11 is an image captured plural times while changing the relative position between the imaging unit 10 and the subject 50 by moving the imaging unit 10 in the X-direction in a state in which a contrast agent has been administered to the subject 50. In this embodiment, the imaging unit 10 is configured to capture a plurality of contrast agent images 11 in a state in which the user is administering a contrast agent to the subject 50 from the foot base toward the toe.

In a state in which a contrast agent has been administered to the subject 50, the X-ray source 1 is configured to emit X-rays to the subject 50. The detection unit 2 is configured to detect X-rays and output a detection signal.

As shown in FIG. 1 and FIG. 4, based on the detection signal, the image processing unit 3 is configured to generate a contrast agent image 11. The generated contrast agent image 11 is configured to be input to the first processing unit 31 and the second processing unit 32 every time it is generated.

As shown in FIG. 4, the image processing unit 3 is configured to subject the contrast agent image 11 input to the first processing unit 31 to first image processing 33 that makes the blood vessel 50a, which is an imaging target, unclear to generate a defocus image 19 in which the blood vessel 50a is made unclear and a portion other than the blood vessel 50a (e.g., bone 50b) is made clear from the contrast agent image 11. In FIG. 4, the uncleared blood vessel 50a is indicated by a broken line.

The image processing unit 3 is configured to perform processing of removing high-frequency components from the contrast agent image 11 by using, for example, a low-pass filter, as first image processing 33. With this, the blood vessel 50a, which is a high-frequency component, is removed to become unclear, so that the defocus image 19 is generated.

Figure 5:
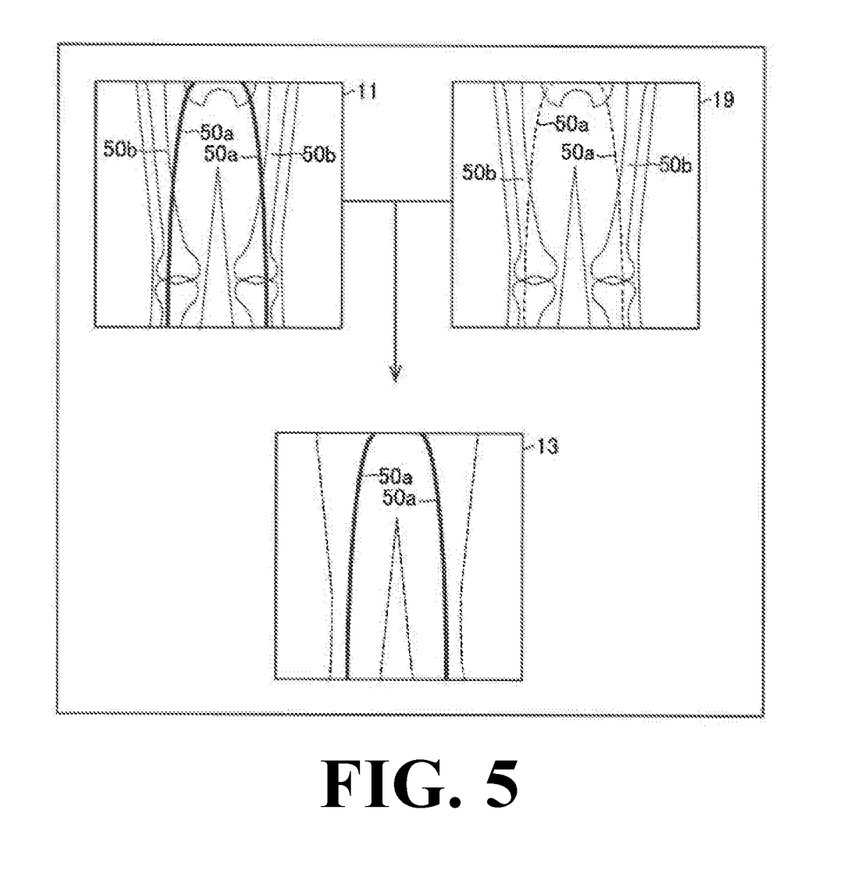
FIG. 5 is a diagram for explaining generation of a first image.

As shown in FIG. 5, the image processing unit 3 is configured to subtract the defocus image 19 from the contrast agent image 11 to produce a first image 13 in which a portion other than the blood vessel 50a is made unclear and the blood vessel 50a is made clear. By subtracting the defocus image 19 from the contrast agent image 11, the pixel value of the portion (portion other than the blood vessel 50a) common to the contrast agent image and the defocus image 19 becomes 0 or near 0. Therefore, by performing the subtraction processing, the portion common to the contrast agent image 11 and the defocus image 19 (portion other than the blood vessel 50a) becomes unclear.

As shown in FIG. 1 and FIG. 2, the control unit 4 is configured to perform control to display the first image on the display unit 7 as soon as the first image 13 is generated by the image processing unit 3 when capturing the contrast agent image 11 while changing the relative position between the imaging unit 10 and the subject 50. The control unit 4 is configured to perform control to sequentially display the first image 13 on the display unit 7 every time it is generated.

Figure 6:
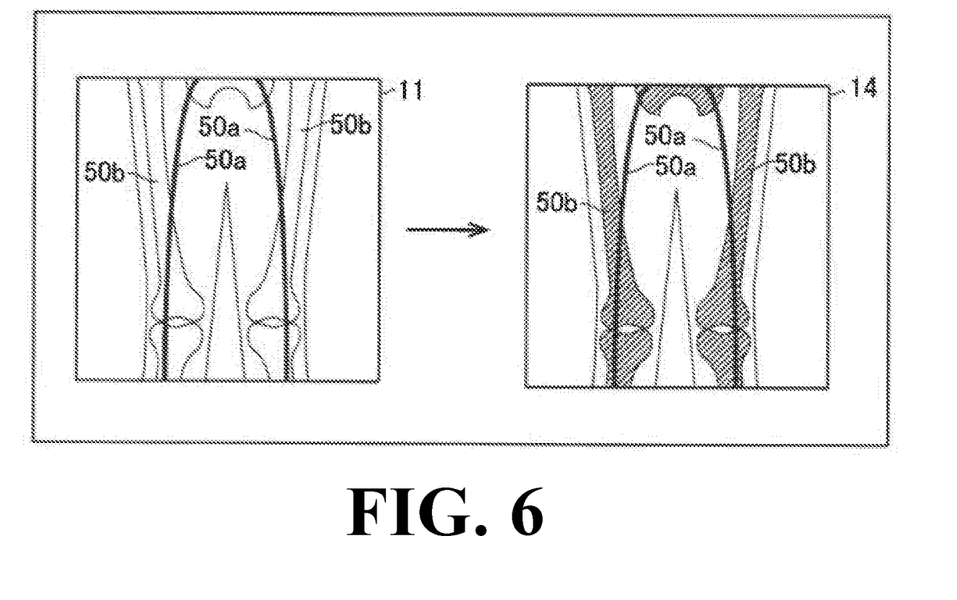
FIG. 6 is a diagram for explaining generation of a second image.

As shown in FIG. 6, the second processing unit 32 of the image processing unit 3 is configured to perform the second image processing 34 that reduces the pixel value difference of a portion of the subject 50 (e.g., bone 50b) common to the contrast agent image 11 and the non-contrast agent image 12 on the contrast agent image 11. The image processing unit 3 inputs the contrast agent image 11 to the first processing unit 31 and the second processing unit 32 each time the contrast agent image 11 is generated. The image processing unit 3 is configured to perform the first image processing 33 and the second image processing 34 in parallel. The image processing unit 3 is configured to generate a second image 14 used to generate a differential long image 18 by performing the second image processing 34.

The image processing unit 3 is configured to perform gradation processing of the contrast agent image 11 as the second image processing 34 based on a preset parameter.

Note that in FIG. 6, the bones 50b are hatched to indicate that the gradation processing has been performed.

The control unit 4 is configured to perform control to store a plurality of second images 14 captured from the foot base to the toe of the subject 50 while changing the relative position between the subject 50 and the imaging unit 10 in the storage unit 8.

(Capturing of Non-Contrast Agent Image)

The control unit 4 is configured to control the imaging unit 10 to store the imaging condition at the time of capturing the contrast agent image 11 and capture a non-contrast agent image 12 based on the stored imaging condition. The imaging condition includes a radiation dose at the time of imaging, an imaging start position, imaging timing, and a relative position between the X-ray source 1, the detection unit 2, and the top board 5. The control unit 4 is configured to control the imaging unit 10 so as to capture the non-contrast agent image 12 under the same imaging condition as the imaging condition, such as, e.g., the radiation dose, the imaging start position, the imaging timing at the time of capturing the contrast agent image 11.

The imaging of the non-contrast agent image 12 is performed in a state in which no contrast agent has been administered to the subject 50. The detection unit 2 is configured to detect X-rays that have passed through the subject 50 and output a detection signal.

The image processing unit 3 is configured to generate a non-contrast agent image 12 based on the detection signal. The non-contrast agent image 12 is input to the first processing unit 31 and the second processing unit 32 of the image processing unit 3 each time it is generated.

As shown in FIG. 7, the second processing unit 32 of the image processing unit 3 is configured to perform the third image processing 35 that reduces the pixel value difference of the portion of the subject 50 (e.g., bone 50b) common to the contrast agent image 11 and the non-contrast agent image 12 on the non-contrast agent image 12. The image processing unit 3 is configured to generate a third image 15 used to generate a differential long image 18 by performing the third image processing 35 on the non-contrast agent image 12.

In the same manner as in the second image processing 34, the image processing unit 3 is configured to perform gradation processing of the non-contrast agent image 12 as the third image processing 35 based on the same parameters as those in the preset second image processing 34. Note that in FIG. 7, the bones 50b are hatched to indicate that the gradation processing has been performed.

As shown in FIG. 8, the image processing unit 3 generates a third image 15 each time a non-contrast agent image 12 is generated. A differential image 17 is generated based on the generated third image 15 and the second image 14 having the same position coordinate as that of the generated third image 15. The differential image 17 becomes an image in which the blood vessel 50a is clearly reflected because the portion common to the second image 14 and the third image 15 (portion other than the blood vessel 50a) is removed by subtracting the third image 15 from the second image 14. The differential image 17 is generated each time the third image 15 is generated, and is sequentially displayed on the display unit 7 each time it is generated.

Figure 9:
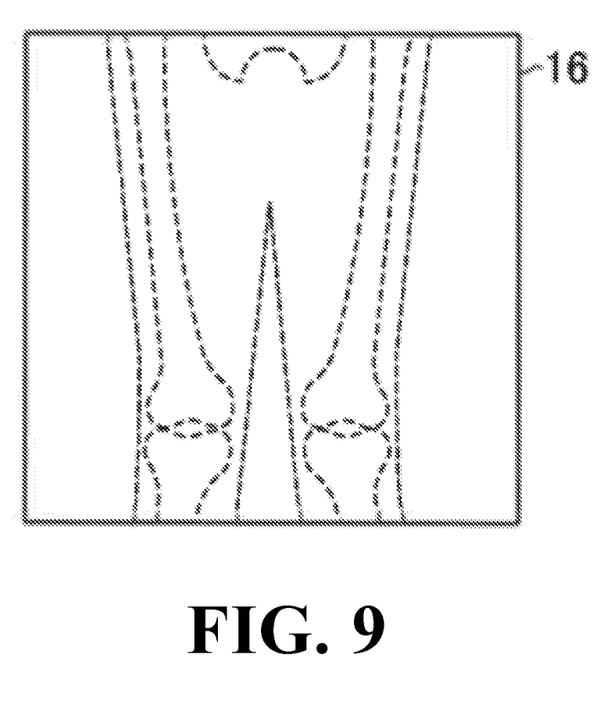
FIG. 9 is a diagram for explaining a fourth image.

As shown in FIG. 9, the first processing unit 31 of the image processing unit 3 is configured to perform fourth image processing 36 to generate a fourth image 16 indicating a contour of a portion other than the blood vessel in the non-contrast agent image 12.

The image processing unit 3 is configured to, as fourth image processing 36, to generate an image in which processing of removing high-frequency components from the non-contrast agent image 12 using, for example, a low-pass filter has been performed. In addition, the image processing unit 3 is configured to generate the fourth image 16 by subjecting an image from which the high-frequency components have been removed and a non-contrast agent image 12 to subtraction processing. Note that since the fourth image 16 is relatively unclear compared with other images, it is illustrated by a broken line in FIG. 9.

The control unit 4 is configured to perform control to store the fourth image 16 in the storage unit 8. The fourth image 16 is used to confirm a contour of a portion other than the blood vessel 50a.

As shown in FIG. 10, the image processing unit 3 generates a differential long image 18 by connecting differential images 17. The image processing unit 3 is configured to generate a differential long image 18 by connecting the differential images 17 in the order of the relative position coordinates of the top board 5 based on the relative position coordinates of the top board 5.

The control unit 4 is configured to perform control to sequentially display a differential image 17 (see FIG. 8) obtained by subjecting the third image 15 and the second image 14 generated by the image processing unit 3 to subtraction processing when capturing a non-contrast agent image 12 while changing the relative position between the imaging unit 10 and the subject 50 (see FIG. 8) to subtraction processing on the display unit 7.

(Capturing of Differential Long Image)

Figure 11:
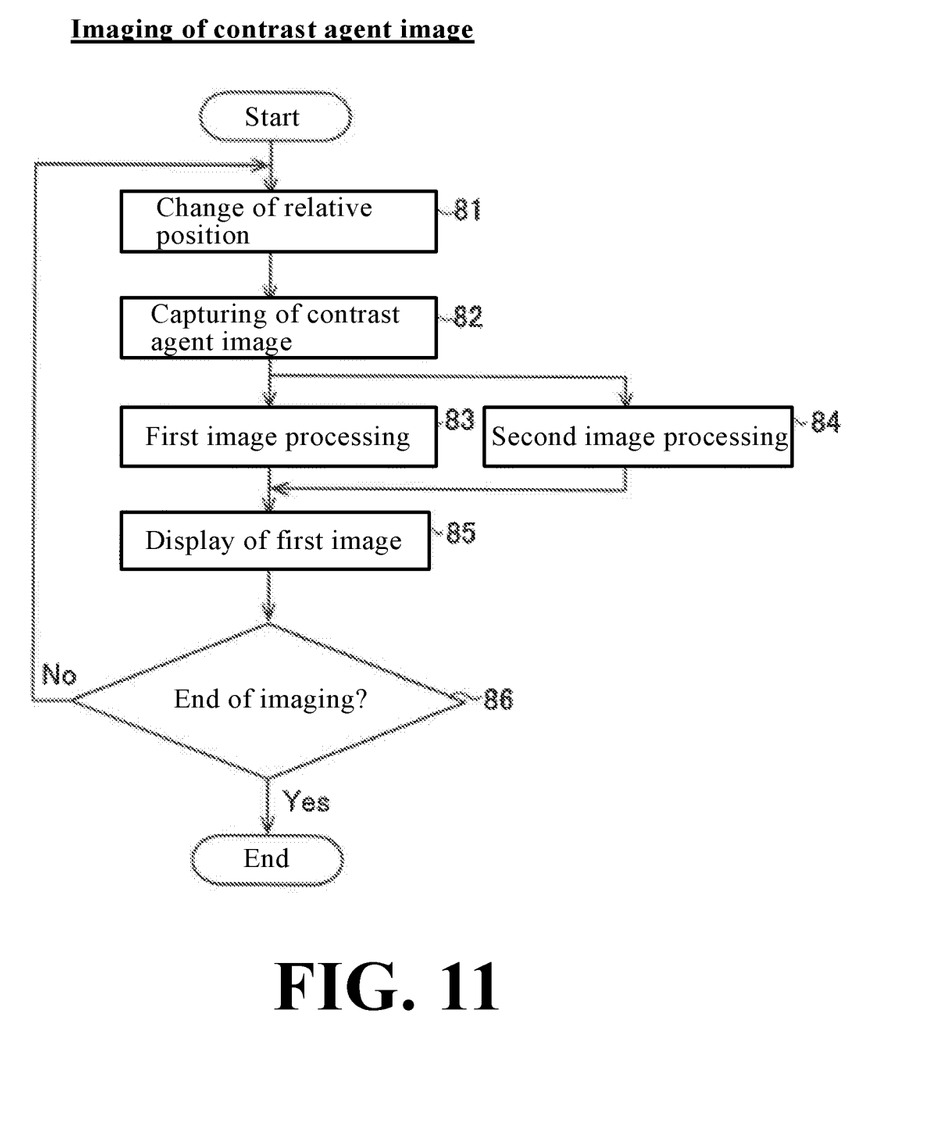
FIG. 11 is a flowchart for explaining generation of a contrast agent image.
Figure 12:
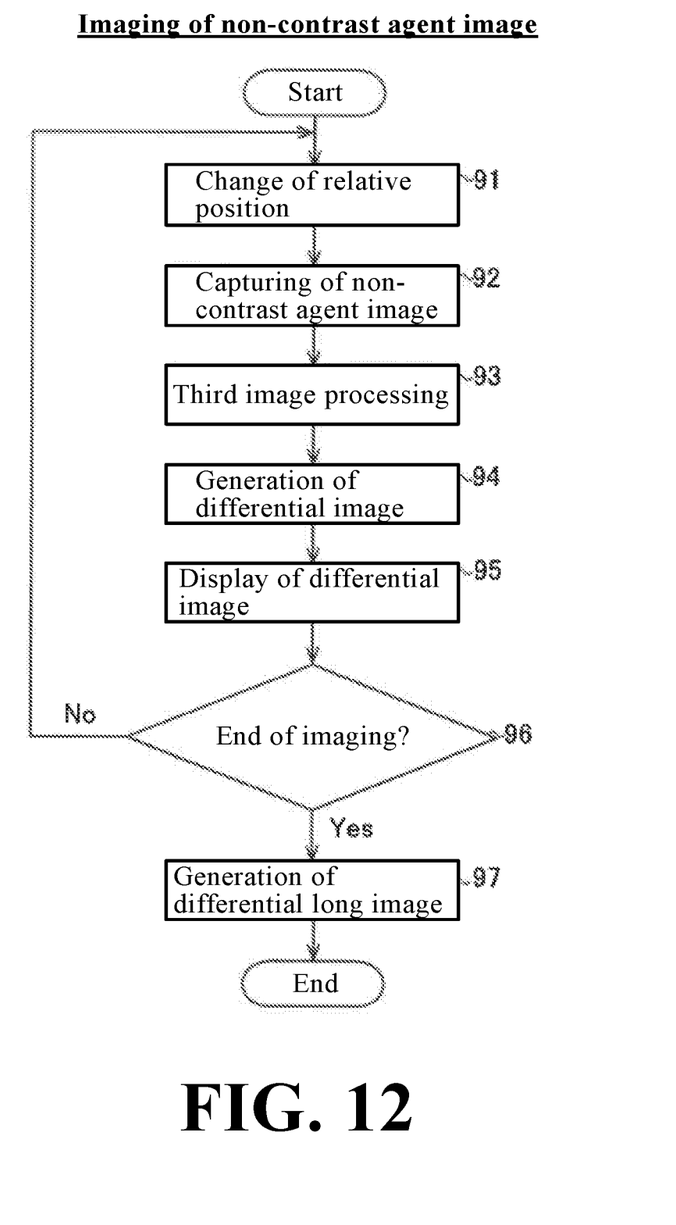
FIG. 12 is a flowchart for explaining generation of a differential long image.

Referring to FIG. 11 and FIG. 12, the operation of the X-ray fluoroscopic imaging apparatus 100 for capturing a differential long image 18 in which the blood vessel 50a of the lower limb of the subject 50 is set as an imaging target will be described.

As shown in FIG. 11, the X-ray fluoroscopic imaging apparatus 100 is configured to initiate capturing of a contrast agent image 11 upon receipt of an input from a user. The capturing of the contrast agent image 11 is performed while administering a contrast agent to a blood vessel 50a of a lower limb of the subject 50.

In Step 81, the X-ray fluoroscopic imaging apparatus 100 is configured to change the relative position between the subject 50 and the imaging unit 10 by moving the top board 5.

In Step 82, it is configured such that X-rays are emitted to the subject 50 from the X-ray source 1 to capture a contrast agent image 11. The detection unit 2 is configured to detect X-rays that have passed through the subject 50 and output a detection signal. The image processing unit 3 is configured to generate a contrast agent image 11 based on a detection signal output from the detection unit 2. The generated contrast agent image 11 is configured to be output to the first processing unit 31 and the second processing unit 32.

In Step 83, the first processing unit 31 is configured to perform the first image processing 33 on the captured contrast agent image 11. The first processing unit 31 is configured to pass the contrast agent image 11 through a low-pass filter as the first image processing 33 to generate a defocus image 19. The first processing unit 31 is configured to generate a first image 13 by subjecting the defocus image 19 and the contrast agent image 11 to subtraction processing.

In Step 84, the second processing unit 32 is configured to perform the second image processing 34 simultaneously with the first image processing 33. At this time, the second processing unit 32 is configured to generate a second image 14 by subjecting the contrast agent image 11 to gradation processing as the second image processing 34. The generated second image 14 is stored in the storage unit 8.

In Step 85, the control unit 4 is configured to perform control to output the generated first image 13 to the display unit 7 and display the same. With this, the user can perform image capturing while confirming whether or not a contrast agent has been sufficiently contained in the blood vessel 50a of the lower limb.

In Step 86, the X-ray fluoroscopic imaging apparatus 100 is configured such that, when an input of ending the capturing operation of the contrast agent image 11 from the user is received, the X-ray fluoroscopic imaging apparatus 100 ends the capturing operation of the contrast agent image 11. When there is no input from the user, the process returns to Step 81, and the X-ray fluoroscopic imaging apparatus 100 is configured to change the relative position between the imaging unit 10 and the subject 50 by moving the top board 5.

As shown in FIG. 12, the X-ray fluoroscopic imaging apparatus 100 is configured to initiate the capturing operation of the non-contrast agent image 12 upon receipt of an input from the user. At the time of capturing a non-contrast agent image 12, no contrast agent has been administered to the blood vessel 50a of the lower limb of the subject 50.

In Step 91, the X-ray fluoroscopic imaging apparatus 100 is configured to change the relative position between the subject 50 and the imaging unit 10 by moving the top board 5.

In Step 92, it is configured such that X-rays are emitted to the subject 50 from the X-ray source 1 to capture a contrast agent image 11. The detection unit 2 is configured to detect X-rays that have passed through the subject 50 to output a detection signal. The image processing unit 3 is configured to generate a non-contrast agent image 12 based on the detection signal output from the detection unit 2. The generated non-contrast agent image 12 is configured to be output to the first processing unit 31 and the second processing unit 32.

The imaging unit 10 is configured to capture a non-contrast agent image 12 under the same imaging condition as that of the contrast agent image 11. The X-ray fluoroscopic imaging apparatus 100 is configured to store the imaging condition such as a radiation dose, an imaging start position, an imaging timing at the time of capturing the contrast agent image 11 in the storage unit 8 and perform capturing of the non-contrast agent image 12 based on the stored imaging condition.

In Step 93, the image processing unit 3 is configured to perform the third image processing 35 on a non-contrast agent image 12. The image processing unit 3 is configured to subject a non-contrast agent image 12 to gradation processing so that the pixel value difference of the portion common to the contrast agent image 11 and the non-contrast agent image 12 becomes small in the same manner as in the second image processing 34, as the third image processing 35.

In Step 94, the image processing unit 3 is configured to generate a differential image 17 from the second image 14 and the third image 15 stored in the storage unit 8. The control unit 4 is configured to subject the third image 15 and the second image 14 captured at the same imaging position as that of a third image 15 generated by the image processing unit 3 out of the second image 14 stored in the storage unit 8 to subtraction processing. The image processing unit 3 is configured to generate a differential image 17 by subtracting the third image 15 from the second image 14.

In Step 95, the control unit 4 performs control to display the differential image 17 on the display unit 7. Thus, the user can perform capturing of a non-contrast agent image 12 while confirming the displayed differential image 17.

In Step 96, when the X-ray fluoroscopic imaging apparatus 100 receives an input of ending capturing of a non-contrast agent image 12 from a user, the X-ray fluoroscopic imaging apparatus 100 ends capturing of the non-contrast agent image 12 and the processing moves to Step 97. If there is no input from the user, the process returns to Step 91, and the X-ray fluoroscopic imaging apparatus 100 is configured to change the relative position between the imaging unit 10 and the subject 50 by moving the top board 5.

In Step 97, the image processing unit 3 is configured to generate a differential long image 18 by connecting differential images 17 in the order of the relative position coordinates of the top board 5 based on the relative position coordinates of the top board 5.

Effects of Embodiment

In this embodiment, the following effects can be obtained.

In the X-ray fluoroscopic imaging apparatus 100 of this embodiment, the image processing unit 3 is configured to generate the first image 13 by performing the first image processing 33 for clarifying the blood vessel 50a as an imaging target with respect to a plurality of contrast agent images 11. The control unit 4 is configured to sequentially display the first image 13 corresponding to each of the contrast agent images 11 when capturing a plurality of contrast agent images 11 while changing the relative position between the imaging unit 10 and the subject 50 and perform control by performing the second image processing 34 that reduces the pixel value difference of a portion of the subject common to the contrast agent image 11 and the non-contrast agent image 12. With this, when capturing a plurality of contrast agent images 11 while changing the relative position between the imaging unit 10 and the subject 50, the first image 13 in which the blood vessel 50a as an imaging target corresponding to each of the contrast agent images 11 is clarified is generated and displayed, so that the user can clearly confirm the moving of the contrast agent in the blood vessel 50a at the time of capturing the contrast agent image 11. In addition, by generating a plurality of second images 14 used to generate a differential long image 18, the differential image 17 can be generated at the time of capturing the non-contrast agent image 12, so that the blood vessel 50a can be confirmed at the time of capturing the non-contrast agent image 12. As a result, a desired differential long image 18 can be appropriately generated.

In this embodiment, the image processing unit 3 is configured to generate a plurality of third images 15 used to generate a differential long image 18 by performing the third image processing 35 that reduces the pixel value difference of the portion of the subject 50 common to the contrast agent image 11 and the non-contrast agent image 12 with respect to a plurality of non-contrast agent images 12 and generate a differential long image 18 from a plurality of second images 14 and a plurality of third images 15. With this, by reducing the pixel value difference of the portion of the subject 50 common to the contrast agent image 11 and the non-contrast agent image 12, in the contrast agent image 11 in which the blood vessel 50a is clear and the non-contrast agent image 12 in which the blood vessel 50a is unclear, the pixel value difference of the common portion other than the blood vessel 50a becomes small between the second image 14 and the third image 15. Therefore, when a differential long image 18 is generated, the common portion other than the blood vessel 50a becomes unclear. As a result, a differential long image 18 in which the blood vessel 50a is clear can be generated.

In this embodiment, the contrast agent image 11 and the non-contrast agent image 12 are the same in the imaging condition, such as, e.g., a radiation dose at the time of imaging, an imaging start position, and an imaging timing, and the image processing unit 3 is configured to perform gradation processing on the contrast agent image 11 as the second image processing 34 and perform gradation processing on the non-contrast agent image 12 as the third image processing 35. With this, since the contrast agent image 11 and the non-contrast agent image 12 are the same in the imaging condition, the contrast agent image 11 and the non-contrast agent image 12 are substantially the same image except for the difference in whether or not the blood vessel 50a is clear. Further, by adjusting the pixel value by performing the gradation processing, the pixel value difference between the second image 14 and the third image 15 can be reduced. As a result, it is possible to assuredly make a portion other than blood vessel 50a unclear when a differential long image 18 is generated.

In this embodiment, the control unit 4 is configured to perform control to sequentially display a differential image 17 obtained by subjecting the third image 15 and the second image 14 corresponding to each of the non-contrast agent images 12 to subtraction processing on the display unit 7 when capturing a non-contrast agent image 12 while changing the relative position between the imaging unit 10 and the subject 50. With this, at the time of capturing the non-contrast agent image 12, it is possible to perform the imaging while confirming the differential image 17 in which the blood vessel 50a is clearer than the first image 13.

In this embodiment, the image processing unit 3 is configured to perform fourth image processing 36 for generating an image indicating a contour of a portion other than the blood vessel 50a. As a result, since it is possible to recognize the contour of the bone 50b, etc., when an abnormality occurs in the generated differential long image 18 due to external factors, it is possible to confirm whether or not the third image 15 generated from the same non-contrast agent image 12 has an abnormality by confirming the fourth image 16.

In this embodiment, the image processing unit 3 is configured to perform the same first processing as the first image processing 33 and the fourth image processing 36 and the same second processing as the second image processing 34 and the third image processing 35. With this, the image processing unit 3 can generate four different images by performing two different processing, and therefore, it is possible to suppress complication of the image processing when generating four different images.

In this embodiment, the image processing unit 3 includes a first processing unit 31 for performing first processing on a contrast agent image 11 and a non-contrast agent image 12, and a second processing unit 32 for performing second processing on a contrast agent image 11 and a non-contrast agent image 12. With this, after generating the contrast agent image 11 and the non-contrast agent image 12, four different images can be generated by performing processing in the first processing unit 31 and the second processing unit 32. Therefore, the number of processing units can be reduced as compared with the case in which a processing unit is provided for each image to be generated, so that the configuration of the image processing unit 3 can be simplified.

In this embodiment, the image processing unit 3 is configured to, as the first image processing 33, generate a defocus image 19 in which the blood vessel 50a is made unclear and a portion other than the blood vessel 50a is made clear from the first image processing 33 and generate a first image 13 in which the blood vessel 50a is made clear by subjecting the contrast agent image 11 and the defocus image 19 to subtraction processing. With this, since the first image 13 is clearer in the blood vessel 50a than the first image 13, and therefore the user can clearly confirm the flow of the contrast agent at the time of capturing the contrast agent image 11.

Modifications

It should be noted that the embodiment disclosed herein is to be considered in all respects as illustrative and not restrictive. The scope of the present invention is indicated by claims rather than by the aforementioned description of the embodiment, and the scope of the present invention includes all modifications (changes) within the meaning and scope equivalent to claims.

For example, in the above embodiment, an example is shown in which the radiation fluoroscopic imaging apparatus is an X-ray fluoroscopic imaging apparatus, but the present invention is not limited to this. In the present invention, the radiation fluoroscopic imaging apparatus may be an imaging apparatus utilizing radiation, such as, e.g., gamma rays.

In the above embodiment, an example is shown in which the X-ray fluoroscopic imaging apparatus changes the relative position between the imaging unit and the subject by moving the top board, but the present invention is not limited to this. In this embodiment, the X-ray fluoroscopic imaging apparatus may change the position of the imaging unit and the subject by moving the imaging unit.

In the above embodiment, an example is shown in which the image processing unit is configured to perform processing of removing high-frequency components from a contrast agent image by using a low-pass filter. For example, the image processing unit may be configured to remove high frequency components using a Fourier transform.

In the above embodiment, an example is shown in which the display unit is provided separately from the X-ray fluoroscopic imaging apparatus, but the present invention is not limited to this. In this embodiment, the display unit may be provided on the X-ray fluoroscopic imaging apparatus.

In the above embodiment, an example is shown in which the image processing unit is configured to generate a differential long image by connecting differential images, but the present invention is not limited to this. In the present invention, the image processing unit may be configured to generate a differential long image by subjecting a long image of the second image and a long image of the third image to subtraction processing after generating a long image of the second image and a long mage of the third image.

In the above embodiment, an example is shown in which the first image processing and the fourth image processing are the same and the second image processing and the third image processing are the same, but the present invention is not limited to this. In this embodiment, the first image processing and the fourth image processing may be different, and the second image processing and the third image processing may be different.

In the above embodiment, an example is shown in which the image processing unit includes the first processing unit and the second processing unit, but the present invention is not limited to this. In the present invention, the image processing unit may include the first processing unit, the second processing unit, the third processing unit, and the fourth processing unit in accordance with the first image processing, the second image processing, the third image processing, and the fourth image processing.

In the above embodiment, an example is shown in which the image processing unit is configured to perform gradation processing by setting parameters as the second image processing and the third image processing, but the present invention is not limited thereto. For example, the image processing unit may be binarized by setting a threshold value.

In the above embodiment, an example is shown in which the image processing unit is configured to perform the first image processing and the second image processing at the same time, but the present invention is not limited thereto. For example, the image processing unit may be configured to perform the second image processing after the first image processing.

(Aspect)

It will be understood by those skilled in the art that the above described exemplary embodiments are concrete examples of the following aspects.

Item 1

An imaging unit comprising:

an imaging unit including a radiation source configured to emit radiation to a subject and a detection unit configured to detect radiation emitted from the radiation source and transmitted through the subject and acquire a detection signal;

an image processing unit configured to generate a plurality of contrast agent images based on the detection signal acquired at a plurality of relative positions using a contrast agent, generate a plurality of non-contrast agent images based on the detection signal acquired at the plurality of relative positions without using a contrast agent, and generate a differential long image by subjecting the non-contrast agent images and the contrast agent images to subtraction processing and connection processing; and a control unit configured to perform control to output an image generated by the image processing unit and display the image on a display unit, wherein the image processing unit is configured to, when capturing the plurality of contrast agent images while changing a relative position between the imaging unit and the subject, generate a first image by performing first image processing that clarifies a blood vessel as an imaging target on the plurality of contrast agent images and generate the plurality of second images used to generate the differential long image by performing second image processing that reduces a pixel value difference of a portion of the subject common to the contrast agent image and the non-contrast image, and wherein the control unit is configured to perform control to sequentially display the first image corresponding to each of the plurality of contrast agent images when capturing the plurality of contrast agent images while changing the relative position between the imaging unit and the subject.

Item 2

The radiation fluoroscopic imaging apparatus as recited in the aforementioned Item 1, wherein the image processing unit is configured to generate a plurality of third images used to generate the differential long image by performing third image processing that reduces a pixel value difference of a portion of the subject common to the contrast agent image and the non-contrast agent image on the plurality of non-contrast agent images, and generate the differential long image by the plurality of second images and the plurality of third images.

Item 3

The radiation fluoroscopic imaging apparatus as recited in the aforementioned Item 2, wherein the contrast agent image and the non-contrast agent image are the same in imaging conditions such as a radiation dose at the time of imaging, an imaging start position, and an imaging timing, and wherein the image processing unit is configured to perform gradation processing on the contrast agent image as second image processing and perform gradation processing on the non-contrast agent image as third image processing.

Item 4

The radiation fluoroscopic imaging apparatus as recited in the aforementioned Item 2 or 3, wherein the control unit is configured to perform control to sequentially display a differential image obtained by subjecting the second image and the third image corresponding to each of the plurality of non-contrast agent images to subtraction processing on the display unit when capturing the plurality of non-contrast agent images while changing the relative position between the imaging unit and the subject.

Item 5

The radiation fluoroscopic imaging apparatus as recited in any one of the aforementioned Items 2 to 4, wherein the image processing unit is configured to perform fourth image processing that generates an image indicating a contour of a portion other than a blood vessel.

Item 6

The radiation fluoroscopic imaging apparatus as recited in the aforementioned Item 5, wherein the image processing unit is configured to perform the same first processing as the first image processing and the fourth image processing and perform the same second processing as the second image processing and the third image processing.

Item 7

The radiation fluoroscopic imaging apparatus as recited in the aforementioned Item 6, wherein the image processing unit includes a first processing unit for performing the first processing on the contrast agent image and the non-contrast agent image and a second processing unit for performing the second processing on the contrast agent image and the non-contrast agent image.

Item 8

The radiation fluoroscopic imaging apparatus as recited in any one of the aforementioned Items 1 to 7, wherein the image processing unit is configured to, as the first image processing, generate a defocus image in which the blood vessel is made unclear and a portion other than the blood vessel is made clear from the contrast agent image and generate the first image in which the blood vessel is made clear by subjecting the defocus image and the contrast agent image to subtraction processing.

The invention claimed is:

1. A radiation fluoroscopic imaging apparatus comprising:
an imaging unit including a radiation source configured to emit radiation to a subject and a detection unit configured to detect radiation emitted from the radiation source and transmitted through the subject and acquire a detection signal;
an image processing unit configured to generate a plurality of contrast agent images based on the detection signal acquired at a plurality of relative positions using a contrast agent, generate a plurality of non-contrast agent images based on the detection signal acquired at the plurality of relative positions without using a contrast agent, and generate a differential long image by subjecting the non-contrast agent images and the contrast agent images to subtraction processing and connection processing; and a control unit configured to perform control to output an image generated by the image processing unit and display the image on a display unit, wherein the image processing unit is configured to, when capturing the plurality of contrast agent images while changing a relative position between the imaging unit and the subject, generate a first image by performing first image processing that clarifies a blood vessel as an imaging target on the plurality of contrast agent images and generate a plurality of second images used to generate the differential long image by performing second image processing that reduces a pixel value difference of a portion of the subject common to the contrast agent image and the non-contrast image, and wherein the control unit is configured to perform control to sequentially display the first image corresponding to each of the plurality of contrast agent images when capturing the plurality of contrast agent images while changing the relative position between the imaging unit and the subject.

2. The radiation fluoroscopic imaging apparatus as recited in claim 1, wherein the image processing unit is configured to generate a plurality of third images used to generate the differential long image by performing third image processing that reduces a pixel value difference of a portion of the subject common to the contrast agent image and the non-contrast agent image on the plurality of non-contrast agent images and generate the differential long image by the plurality of second images and the plurality of third images.

3. The radiation fluoroscopic imaging apparatus as recited in claim 2, wherein the contrast agent image and the non-contrast agent image are the same in imaging conditions such as a radiation dose at the time of imaging, an imaging start position, and an imaging timing, and wherein the image processing unit is configured to perform gradation processing on the contrast agent image as the second image processing and perform gradation processing on the non-contrast agent image as third image processing.

4. The radiation fluoroscopic imaging apparatus as recited in claim 2, wherein the control unit is configured to perform control to sequentially display a differential image obtained by subjecting the second image and the third image corresponding to each of the plurality of non-contrast agent images to subtraction processing on the display unit when capturing the plurality of non-contrast agent images while changing the relative position between the imaging unit and the subject.

5. The radiation fluoroscopic imaging apparatus as recited in claim 2, wherein the image processing unit is configured to perform fourth image processing that generates an image indicating a contour of a portion other than the blood vessel.

6. The radiation fluoroscopic imaging apparatus as recited in claim 5, wherein the image processing unit is configured to perform the same first processing as the first image processing and the fourth image processing and perform the same second processing as the second image processing and the third image processing.

7. The radiation fluoroscopic imaging apparatus as recited in claim 6, wherein the image processing unit includes a first processing unit for performing the first processing on the contrast agent image and the non-contrast agent image and a second processing unit for performing the second processing on the contrast agent image and the non-contrast agent image.

8. The radiation fluoroscopic imaging apparatus as recited in claim 1, wherein the image processing unit is configured to, as the first image processing, generate a defocus image in which the blood vessel is made unclear and a portion other than the blood vessel is made clear from the contrast agent image and generate the first image in which the blood vessel is made clear by subjecting the defocus image and the contrast agent image to subtraction processing.

* * * * *